United States Patent [19]

Molner

[11] 3,964,513
[45] June 22, 1976

[54] ROTATING SAMPLING VALVE

[75] Inventor: Stanley Frank Molner, Morristown, N.J.

[73] Assignee: Hoffmann-La Roche Inc., Nutley, N.J.

[22] Filed: Apr. 8, 1975

[21] Appl. No.: 566,634

[52] U.S. Cl.............................. 137/624.18; 222/264; 222/287; 73/422 TC
[51] Int. Cl.².......................................... G01N 1/20
[58] Field of Search.................... 137/624.11, 624.13, 137/624.15, 624.18, 624.2; 222/264, 288, 287; 73/422 GC, 422 R, 421 R, 422 TC

[56] References Cited
UNITED STATES PATENTS

| | | | |
|---|---|---|---|
| 2,472,092 | 6/1949 | Campbell......................... | 222/264 X |
| 2,865,447 | 12/1958 | Kaufman......................... | 222/288 X |
| 3,067,912 | 12/1962 | Neri................................ | 222/370 X |
| 3,080,759 | 3/1963 | McQuaid........................ | 73/422 TC |
| 3,885,439 | 5/1975 | Stone ............................. | 73/422 GC |

*Primary Examiner*—Alan Cohan
*Attorney, Agent, or Firm*—Samuel L. Welt; George M. Gould

[57] ABSTRACT

A rotating sampling valve is described consisting of a rotating plate held between two fixed plates. The rotating plate contains a number of concentric channel sets bored through its longitudinal axis which channels are disposed symmetrically around its center axis. The channels in each set are of equal volume while the volume of channels in different sets can vary as desired. Both the upper and lower fixed plates contain the same number of correspondingly placed channels serving as inlets and outlets. Thus, when the center plate is rotated liquids flowing through the channels in the center plate are entrapped and transferred to a position indexing with different channels in the upper and lower plates. By connecting the desired inlet and outlet channels with selected sets of channels in the rotating plate it is possible to obtain varying sample volumes. This sampling valve is useful in obtaining discontinuous samples from column eluents for analytical assay such as, for example, fluorescence analysis of proteins, peptides and amino acids, or in other chemical analysis, process control and other purposes. Moreover it is possible to readily change the sample volumes obtained without replacement of the valve body.

5 Claims, 2 Drawing Figures

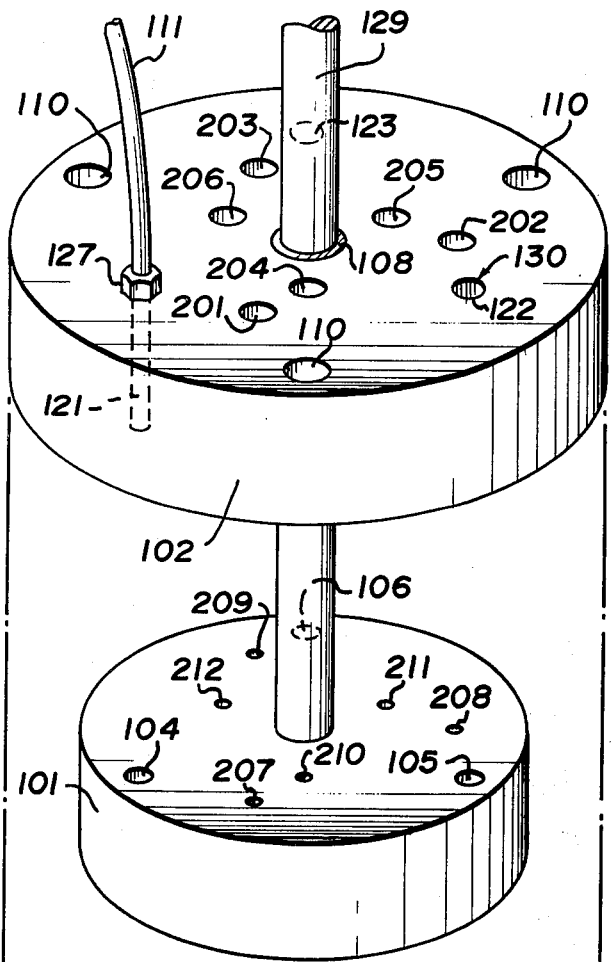
FIG. 1
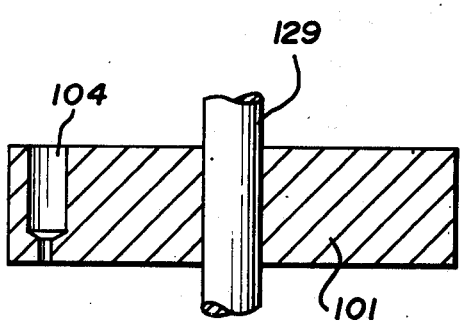
FIG. 2
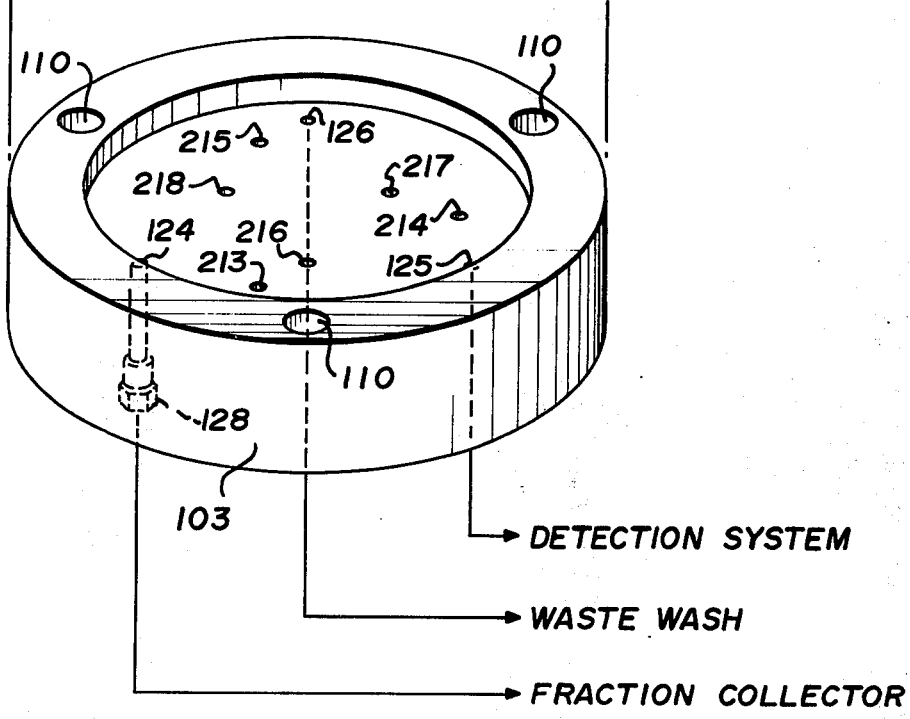
→ DETECTION SYSTEM
→ WASTE WASH
→ FRACTION COLLECTOR

ROTATING SAMPLING VALVE

DESCRIPTION OF THE INVENTION

The present invention relates to a rotating sampling valve useful for obtaining discontinuous samples from liquid streams for analysis. This valve comprises a central cylindrical plate rotating in stepwise fashion by means of a stepping motor, Geneva mechanism or electrically or pneumatically activated solenoid connected thereto by means of a suitable shaft. The central cylindrical plate is clamped between two fixed plates so as to effect a liquid-tight seal between the various plates. The central plate contains a number of channel sets bored through its approximately longitudinal axis, which channel sets are symmetrically disposed about its central axis. In order to provide space between channels of the several sets, so as to make connections easy, the channels of any set are disposed at different azimuths (relative to some zero azimuth reference on the rotating plate) from other sets. The channels in each set are of equal volume while the volume of channels in different sets can vary as desired. Corresponding channels are contained in the upper and lower fixed plates to serve as liquid inlets and outlets. These inlet and outlet channels are threaded in conventional manner allowing for introducing or removing connection tubes as desired. In this manner one can select any one of the available sets of channels thus providing a selection in the volume of the sample collected. By stepwise rotation of the cylindrical central plate, the liquid streams flowing through the channel sets contained therein are entrapped and transferred to positions indexing with other inlet and outlet channels of the upper and lower plates. Thus discrete samples of liquid streams having a volume aproximately that of the channels in the central plates can be collected and transferred to a second stream. Such samples would then be available for other operations the operator wishes to perform on the liquid sample.

The rotary valve of the present invention may be more clearly understood by reference to the drawing which shows a side view of a representative valve. As indicated above, the valve consists of rotating cylindrical plate 101 rotatably mounted and clamped tightly between an upper fixed plate 102 and a lower fixed plate 103. The plates may be constructed out of conventional materials such as polyfluorinated ethylene plastic, e.g., Teflon $^R$ or stainless steel, for example. Most preferably, the rotating plate is made of one of the aforesaid types of materials, e.g., Teflon, and the fixed plates are made of another type, e.g., stainless steel.

Cylindrical plate 101 contains a plurality of channels which are bored parallel to its longitudinal axis. These channels are arranged in concentric sets which are symmetrically disposed about the center axis of plate 101. Each of the channels in a given set is of equal volume while the volume of channels in different sets can vary as desired. Additionally the channels of each set are on different radii from the channels of any other set. It is possible to provide cylindrical plates having from 1 to 36 sets of channels with from 3 to 36 channels in each set.

The representative plate 101 in FIG. 1 is seen to have three sets of channels containing three channels per set. For most uses of the valve of the present invention, the volume of the channels may be in the range of from 5 to 1000 $\mu$l. The channel sets comprise channels 104, 105 and 106 as one set lying concentrically most distant from the center; channels 207, 208 and 209 as a second set lying concentrically an intermediate distance from the center; and channels 210, 211 and 212 as the third set lying concentrically closest to the center.

In an embodiment of the invention wherein said improved rotating valve is employed to provide discontinuous samples from column eluents for analytical assay suitable dimensions and volumes of the channels may be as set forth in the following table:

| Channels | Volume ($\mu$l) | Diameter (in.) | Radial Position (in.) |
|---|---|---|---|
| 104, 105, 106 | 40 each | .1110 | .860 |
| 207, 208, 209 | 20 each | .0785 | .680 |
| 210, 211, 212 | 10 each | .0550 | .530 |

The surfaces between the upper and lower fixed plates and cylindrical plate 101 are machined to a smooth, low friction finish so as to minimize friction and facilitate rotation of cylindrical plate 101. Moreover, when the three plates are clamped tightly together these surfaces provide a liquid-tight seal to prevent leakage of liquid between the channels and the plates. Thus, in operating condition plate 101 is clamped tightly between fixed plates 102 and 103 using suitable clamping means provided through holes 110. To facilitate clamping the diameter of the fixed plates 102 and 103 should be somewhat greater than the diameter of the rotating cylindrical plate 101. Clamping of the plates does not prevent the rotation of cylindrical plate 101.

Rotation of cylindrical plate 101 is accomplished using conventional stepping motor means (not shown) which is connected to said plate through shaft 129. Suitable conventional stepping motor means include stepping motor, pneumatically or electrically activated solenoid-cams systems, Geneva mechanisms, and the like. This shaft passes through plate 102 by means of a suitable central hole 108. The stepping motor means is of conventional design and construction and turns the shaft one position or step when activated by an electrical signal. Thus, the indexing $=1/n$th of a revolution, where n = number of holes per set.

In the specific embodiment shown in the drawing, cylindrical plate 101 contains three channel sets which channel sets contain three channels which are each disposed at an angle of 120° from the other channels in the same set. Both the upper and lower fixed plates each contain corresponding placed channel sets of three channels each at positions (121, 122, 123); (201, 202, 203); (204, 205, 206); (124, 125, 126); (213, 214, 215) and (216, 217, 218). These channel sets are arranged in such a position as to index with the channel sets in plate 101 when cylindrical plate 101 rotates around its longitudinal axis so as to provide a continuous liquid flow path through the channel sets in the three plates when the index position is reached.

Thus, in the specific embodiment described in the drawing, the stepping motor provided will have a step of 120°. It is obvious that if the number of channels in each set is changed such as, for example, to 6 or even 36 then the step of the stepping motor will be adjusted accordingly, such as to 60° or 10°, respectively.

In the embodiment depicted in FIG. 1, the operator has selected to employ the sample volume represented by channels 104, 105 and 106 of plate 101. To render such channel set operative, connector means 127 and 128 are introduced into channels 121 and 124 respectively which are indexed with channel 104 and provide a continuous liquid flow path through the valve. It is understood that similar connectors (not shown for purposes of simplicity) are introduced into channels 122 and 123 of plate 102 and channels 125 and 126 of plate 103.

During operation of the subject valve, a first liquid stream passes through channel 104, entering through inlet 111 and channel 121 via plastic connector 127 in upper plate 102 and exiting through outlet channel 124 via plastic connector 128 to whatever end use or collection device, i.e., fraction collector, desired by the operator. It is to be noted that inlet channel 121 and outlet channel 124 are in direct flow relationship with channel 104 in this position of the operating cycle.

When the stepping motor is activated by a suitable signal provided from an external source, such as an automatic fraction collector for example, the stepping motor indexes one step. In the embodiment shown such step would be a total of 120°. This indexing causes a similar rotation of cylindrical plate 101. Thus, channel 104, when said rotation is complete, is placed in direct flow relationship with channel 122 of top plate 102 and channel 125 at bottom plate 103. The rotation from the first discussed position causes the entrapment and the transfer of a sample of the liquid stream approximately equal in volume to that of channel 104.

In the second position in the cycle which involves counter-clockwise rotation as viewed from top, a second liquid stream enters into channel 130 in top plate 102 and washes out the entrapped sample in channel 104 through outlet channel 125 for uses appropriate with the system in which the said valve is employed, i.e., a fluorescence detection system when the valve is used in a protein or peptide analyzer.

Upon the next index signal to the stepping motor, cylindrical plate 101 rotates another 120°. At this point in the cycle, channel 104 is in direct flow relationship with channel 123 in top plate 102 and outlet channel 126 in bottom plate 103. A third liquid stream such as, for example, a wash solution passes through channel 104 in this position to ensure that the channel is free from any residual contamination from the first and second liquid streams from the prior cycles when channel 104 returns to its initial position. The wash liquid exits from the valve through outlet channel 126. On the next indexing signal, the stepping motor is again activated and another rotation of 120° is made by cylindrical plate 101 so as to return channel 104 to its original position in the cycle, that is, in direct flow relation with channels 121 and 124. It is understood, of course, that channels 105 and 106 will follow the same cycle as channel 104 except that they are 240° and 120° out of phase, respectively with channel 104. Thus, when channel 104 is in position to pass the first liquid stream, then channel 106 is passing the wash solution and channel 105 is passing the second liquid stream.

When it is desired to utilize a different sample volume the valve operation is stopped and the connectors in plate 102 are removed and introduced into another channel set, i.e., either (201, 202, 203) or (204, 205, 206). The channels in plate 102 and 103 are of equal size to facilitate the interchangeability of the connectors. Similar adjustments are made to render the corresponding channel set operational in plate 103. In this manner the instant valve can be quickly converted from one sample volume to another without requiring removal of the entire valve mechanism from the system in which it is contained.

While the various liquid streams are shown in FIG. 1 to flow from top to bottom, such flow direction is not critical. Thus, the inlets can be provided at the bottom of the valve and the outlets at the top without departing from the spirit of the present invention. In addition, rotation of the valve can be clockwise or counterclockwise as desired.

The rotating sampling valve of the present invention is of particular usefulness in providing discontinuous sampling for a protein monitor described in U.S. Pat. application Ser. No. 470,422, entitled "Protein Monitor," inventor, Peter Bohlen, filed May 16, 1974.

When used in conjunction with the aforesaid protein monitor, the rotating sample valve of the present invention can be adapted with a plurality of channels in each set in excess of the three shown in the present preferred embodiment. Preferably, such plurality will comprise a multiple of three. Each triad of contiguous channels of each set in the valve could thus be adapted to receive through appropriate inlets in the upper plate channels of a sample liquid stream, a buffer solution for carrying the sample to the detector and a water wash stream, respectively. In this manner, it would be possible to monitor several sample streams simultaneously.

FIG. 2 represents a diammetrical cross-sectional view of plate 101 which disects one of the channels therein. This figure describes a preferred embodiment in the construction of the channels used in the rotating plate.

As seen herein the channels whose volume determines the sample collected by the valve, are comprised of a cylindrical section at the top, a truncated cone within the rotating plate and a smaller cylinder at the bottom. The purpose of this design is to assure that no fluid is caught in the calibrated volumes of the rotating plate channels and that the sample fluids will thus be made to drain completely.

Such channels may be conveniently constructed by drilling the channel from the top but only part way through. Then a hole approximately 0.012 inch is drilled from the bottom to complete the passageway for fluid. Thus, consistency of sample size within reasonable limits of measurement can be attained by the valve of the present invention.

I claim:

1. In a rotating sample valve comprising:
   a. a cylindrical plate containing a plurality of channels parallel to its longitudinal axis, said channels being symmetrically disposed about the center axis of said cylindrical plates;
   b. an upper and lower fixed plate between which said cylindrical plate is rotatably mounted, said upper plate and lower plate each containing the same plurality of channels symmetrically disposed around their respective center axis so that such channels are in operative flow relation with corresponding channels in said cylindrical plate;
   c. a stepping motor means which is operatively connected to said cylindrical plate;

the improvement which comprises providing said channels in said cylindrical plate in a number of concentric sets the channels of any set being disposed at a different azimuth from the channels of the other sets wherein the volume of the channels in each set is equal while the volume of the channels in different sets may vary, providing corresponding channel sets in said upper and lower fixed plates, providing detachably attached inlet and outlet means to one of the sets of channels in each of the said upper and lower plates respectively which correspond with a channel set in said cylindrical plate thus allowing the selection of a variable sample volume from the volumes of the channels in each of said channel sets in said cylindrical plate and providing said stepping motor means with a step proportional to the number of channel sets.

2. The improved valve of claim 1 wherein three channel sets are provided in each of said plates.

3. The improved valve of claim 1 wherein the channels in said cylindrical plate have a volume in the range of from 5 to 1000 µl.

4. The improved valve of claim 1 wherein the channels in said cylindrical plate have a cylindrical section at the top, a truncated cone within said plate and a smaller cylindrical section at the bottom so as to provide complete draining of the channel.

5. The improved valve of claim 1 wherein said detachably attached inlet and outlet means are plastic connectors and said channels in said upper and lower plates are tapped to receive said connectors.

* * * * *